United States Patent
Delaney

(10) Patent No.: US 8,354,071 B2
(45) Date of Patent: Jan. 15, 2013

(54) STERILISER

(75) Inventor: Martina Maria Delaney, Dublin (IE)

(73) Assignee: Handy Baby Products Limited, Coolock Dublin (IE)

( * ) Notice: Subject to any disclaimer, the term of this patent is extended or adjusted under 35 U.S.C. 154(b) by 510 days.

(21) Appl. No.: 12/451,771

(22) PCT Filed: May 19, 2008

(86) PCT No.: PCT/EP2008/004003
§ 371 (c)(1),
(2), (4) Date: Nov. 30, 2009

(87) PCT Pub. No.: WO2008/145272
PCT Pub. Date: Dec. 4, 2008

(65) Prior Publication Data
US 2010/0166618 A1   Jul. 1, 2010

(30) Foreign Application Priority Data
May 31, 2007   (IE) .................................. S2007/0394

(51) Int. Cl.
*A61L 2/00* (2006.01)
*B08B 3/00* (2006.01)
*H05B 6/64* (2006.01)

(52) U.S. Cl. ........ 422/292; 422/279; 422/300; 422/302; 422/305; 134/102.1; 219/682; 219/401; 261/DIG. 10; 261/DIG. 76

(58) Field of Classification Search .................... 422/26, 422/279–300, 302, 305; 134/30, 102.1; 219/682, 219/401; 261/DIG. 10, DIG. 76
See application file for complete search history.

(56) References Cited

U.S. PATENT DOCUMENTS 5,213,776 A * 5/1993 Maniero et al. ............... 422/303

* cited by examiner

*Primary Examiner* — Jill Warden
*Assistant Examiner* — Monzer Chorbaji
(74) *Attorney, Agent, or Firm* — Wood, Phillips, Katz, Clark & Mortimer

(57) ABSTRACT

A sterilizing device is described, for sterilizing items through steam sterilization. The device has a base and a cover that couple to form an enclosed space, with an item mount provided within the enclosed space. A portion of water is provided in the base portion, which can be converted to steam in a microwave to sterilize any items placed on the mount. The device further employs several downward-facing valves to provide for the release of steam and the draining of excess or heated water.

14 Claims, 3 Drawing Sheets

STERILISER

FIELD OF THE INVENTION

The invention relates to a device for sterilising items, more particularly a device for sterilising pacifiers.

BACKGROUND TO THE INVENTION

In order to combat the spread of germs and prevent infection in infants, it is common to sterilise various items such as baby pacifiers and bottle teats prior to use. This is often accomplished by bathing the items to be sterilised in a disinfectant liquid for a period of time. This requires a certain degree of preparation and planning to ensure a steady supply of sterilised items.

It is known to provide steriliser assemblies for use in microwaves. In general, a steriliser assembly comprises a closed container to hold the items to be sterilised. A portion of water is deposited in the base. The steriliser assembly is then passed through a microwave, which converts the contained water to steam at high temperatures, resulting in steam sterilisation of the contained items.

U.S. Pat. No. 5,213,776 discloses such a steam steriliser for use in a microwave. However, space is limited in the disclosed configuration, and the steam valve used may result in harmful burns to a user of the device.

It is an object of the invention to provide a steriliser device that overcomes the above problems.

SUMMARY OF THE INVENTION

Accordingly, there is provided a device for sterilising items through steam sterilisation, the device comprising:
- a base portion having a receptacle to receive a quantity of water;
- a removable cover portion to substantially cover said receptacle; and
- a mounting portion to receive an item to be sterilised, the mounting portion projecting from said base portion and enclosed beneath said cover portion, wherein the device further comprises a plurality of valves located on said cover portion, the open face of said valves facing in the direction of said base portion, the valves operable to allow steam to exit the device, the valves further operable to allow any excess water to be drained from the device.

The use of the valves prevents serious injury to a user of the device, as they allow steam to escape from the device in a direction away from the user, and they also allow any heated water to be removed safely from the device.

Preferably, the mounting portion comprises a main body and a plurality of mounting arms projecting from the main body, the mounting arms curved in the direction away from said base portion.

Preferably, the device further comprises a plurality of engaging arms located on said base portion, and a plurality of engaging elements located on said cover portion, the position of the engaging elements on the cover portion corresponding to the location of the engaging arms on the base portion, the engaging arms operable to couple with the engaging elements to releasably secure the cover portion to the base portion.

Preferably, the device further comprises a portion of support material located on the underside of the base portion, wherein the support material is non-slip material.

Preferably, the vents are provided on the removable cover portion.

Preferably, a receiving channel is defined on each of said plurality of mounting arms, said receiving channel facing away from said base portion, said receiving channel being to receive a portion of said item to be sterilised.

The use of the receiving channel retains the items to be sterilised in position on the mounting arms, preventing slippages or falls.

Preferably, said plurality of mounting arms projecting from the main body comprises:
- a first plurality of mounting arms arranged about said main body, said first plurality located towards a first free end of said main body; and
- a second plurality of mounting arms arranged about said main body, said second plurality located between said first plurality of mounting arms and said base portion.

Preferably, the orientation of said second plurality of mounting arms about said main body is offset from the orientation of said first plurality of mounting arms about said main body.

As the arms between successive groups are offset, this allows for more efficient mounting of items to be sterilised within the device.

Preferably, said plurality of mounting arms are provided in the form of separate modular components, said plurality of mounting arms releasably coupling to said main body.

Providing the arms as modular components allows for a user of the device to configure the internal arrangement of the mounting arms to their own satisfaction, e.g. more arms if they want to mount more items to be sterilised, or less arms if larger items are being used which require more internal space to be accommodated.

Preferably, said plurality of mounting arms extend from said main body to a free end adjacent an interior surface of said removable cover portion when said removable cover portion is releasably secured to said base portion.

As the arms extend closely to the internal surface of the cover, there is less of a gap presented that the items may fall through, thus reducing the likelihood of slippages and falls, and increasing the suitability of the device for the transportation of the items also.

Preferably, a recess is defined on said removable cover portion, a handle element provided within said recess.

Preferably, said handle is insulated from said removable cover portion.

As the handle is insulated, the relatively high temperatures produced during the steam sterilisation process will not affect a user as they move the device after sterilisation from the location of sterilisation (e.g. a microwave interior) to another location to cool down.

Preferably, said removable cover portion is substantially transparent.

Preferably, said device is formed of material suitable for use in a microwave.

DETAILED DESCRIPTION OF THE INVENTION

An embodiment of the invention will now be described, by way of example only, with reference to the accompanying drawings, in which.

Figure 1:
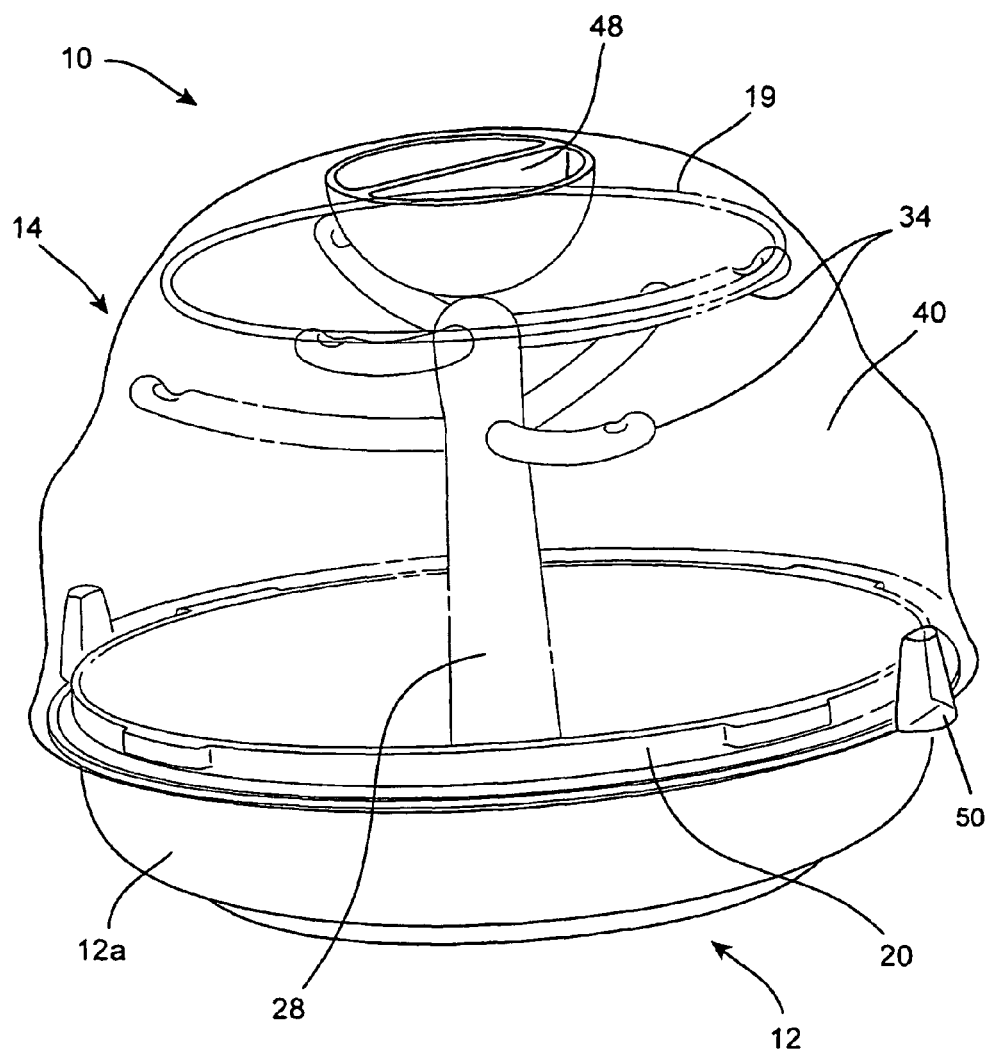
FIG. 1 is a side perspective view of a steriliser according to the invention.

With reference to FIG. 1, a steriliser is indicated generally at 10. The steriliser 10 comprises a base portion 12 and a cover portion 14.

Figure 4:
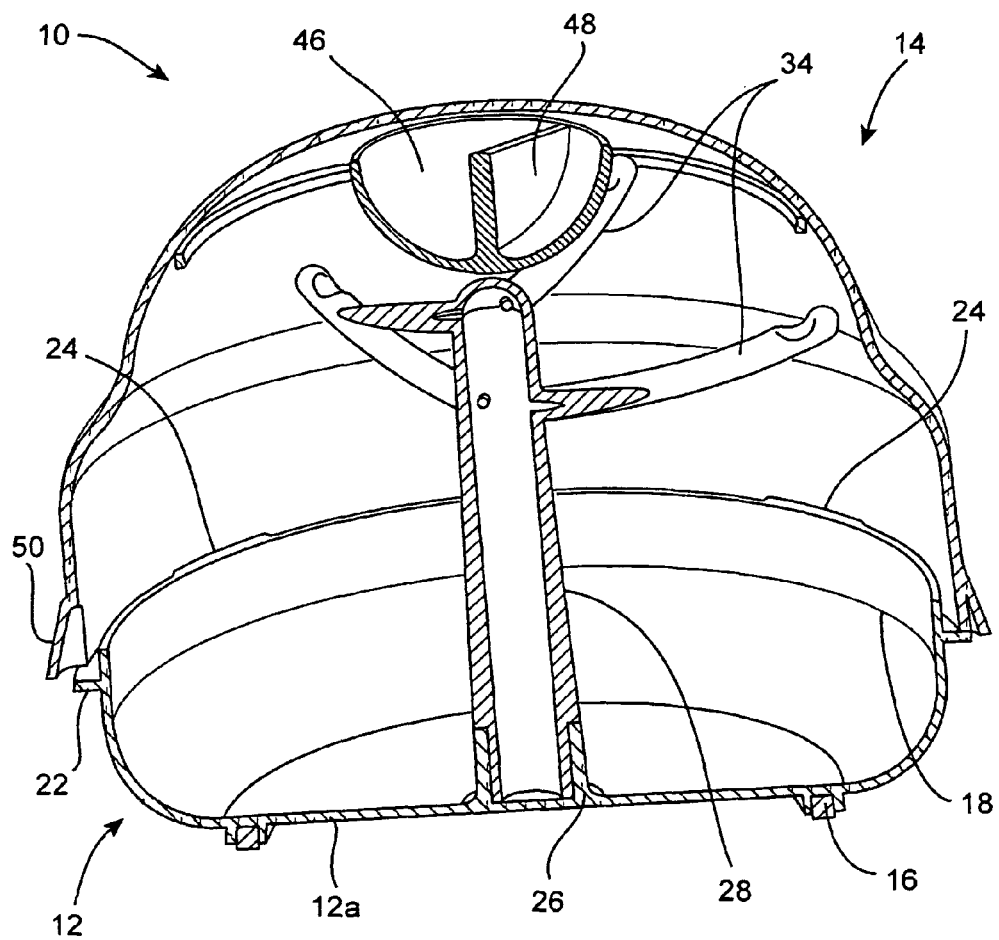
FIG. 4 is a cross-sectional view of the steriliser of FIG. 1.

Base portion 12 comprises a circular bowl-shaped body 12a. The individual detail of the body 12a can be more easily seen in the cross-section shown in FIG. 4. A ring 16, preferably of non-slip material, is provided on the base of the bowl-shaped body 12a. This prevents the steriliser 10 from any unintentional movement during use.

Visual indicator means are provided in the form of a raised fill line 18 on the internal surface of the bowl-shaped body 12a. The fill line 18 provides suggestion as to what level the steriliser 10 should be filled with water prior to use.

A coupling collar 20 extends entirely around the rim of the bowl-shaped body 12a. The coupling collar 20 comprises a shoulder 22 that projects from the external surface of the bowl-shaped body 12a perpendicular to the external surface of the bowl-shaped body 12a. The coupling collar 20 further comprises a plurality of locating projections 24 projecting from the exterior of the collar 20 above the shoulder 22. The locating projections 24 are spaced from the shoulder 22, and are located adjacent the rim of the bowl-shaped body 12a.

A mounting stem 26 is provided on the internal surface of the bowl-shaped body 12a, at the centre-point of the bowl-shaped body 12a. The mounting stem 26 is adapted to receive a tree-shaped mounting portion 28.

Figure 3:
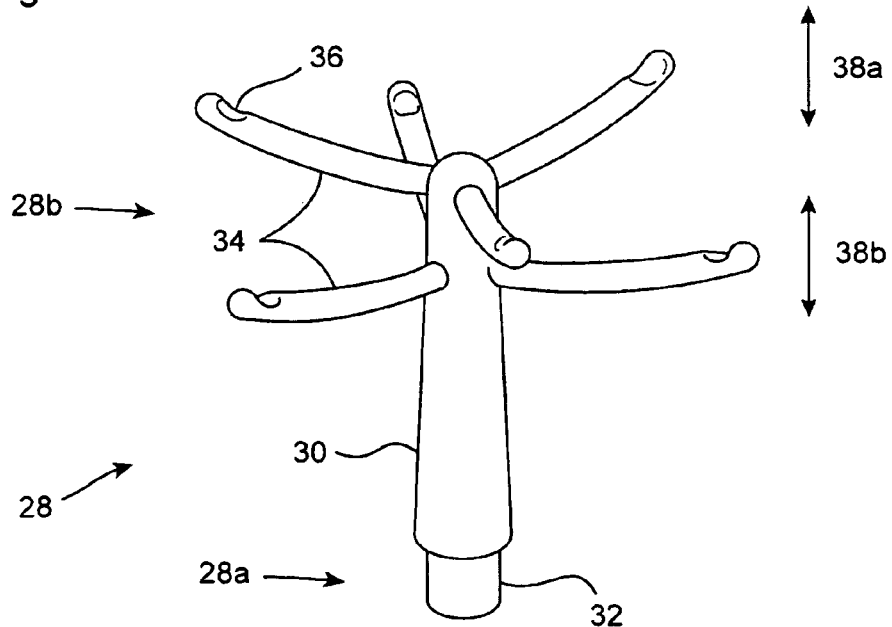
FIG. 3 is an enlarged view of the tree portion of the steriliser of FIG. 1.

Turning to FIG. 3, the tree-shaped mounting portion 28 can be seen in greater detail. The mounting portion 28 has a first base end 28a and a second free end 28b, and comprises a central trunk 30. A pairing portion 32 is located at the base end 28a of the central trunk 30. The pairing portion 32 releasably couples with the locating projections 26 provided in the base portion 12.

A plurality of mounting arms 34 project from the central trunk 30, the arms 34 being located towards the free end 28b of the central trunk 30. The arms 34 are slightly curved in the direction of the free end 28b of the mounting portion 28. A semicircular channel 36 is defined on a portion of each arm 34, at the distal end of each arm 34. The channel 36 is defined on that side of the arm 34 facing in the direction of the free end 28b of the mounting portion 28. The channel 36 can be used to receive the handle of an infant pacifier, to prevent the pacifier from falling off the mounting arms when in use.

In the embodiment shown in the accompanying figures, a total of six arms 34 are provided. The arms 34 are arranged in two groups 38a,38b of three arms 34 each, with the arms 34 in each row 38a,38b separated by 120° from each other. The corresponding arms 34 in the two rows are further staggered, so that the arms 34 in the lower row 38b are 60° out of phase with the arms 34 in the upper row 38a. Use of this configuration results in a maximisation of the available space within the steriliser 10. It will be understood that other configurations of arms may be employed to maximise the available space.

In a further embodiment, the mounting portion 28 may be provided as part of a modular construction that allows for the number of rows of mounting arms 34 to be varied according to the wishes of a user of the steriliser 10. This could be used to accommodate various numbers of pacifiers of different sizes, and other items to be sterilised that would not fit into the steriliser 10 if the original number of mounting arms 34 were present.

Figure 2:
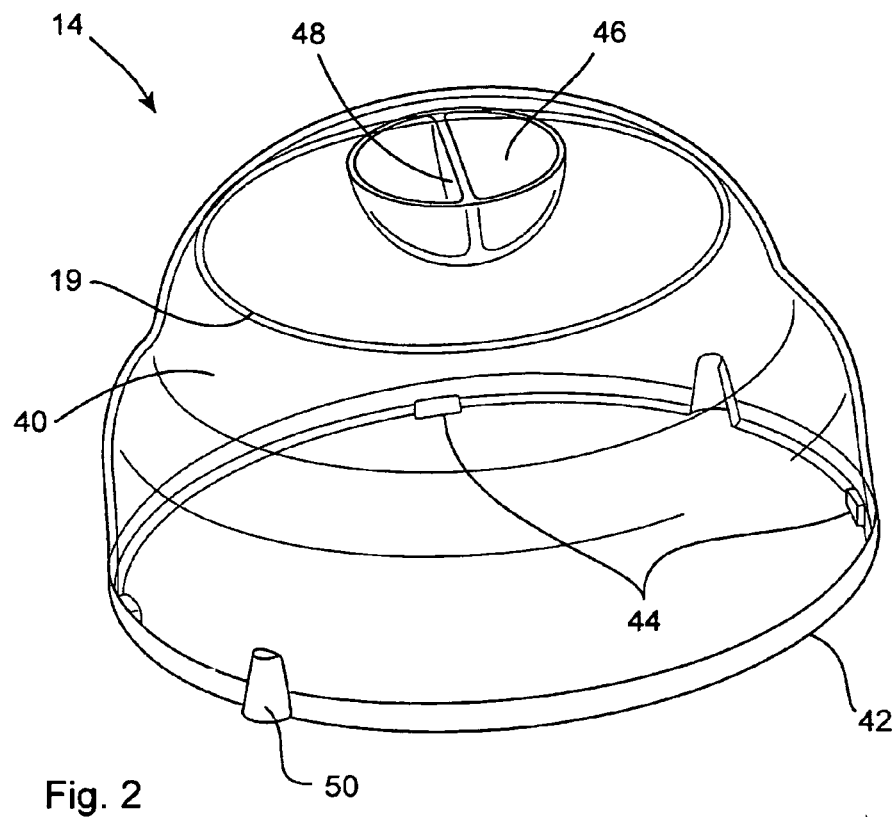
FIG. 2 is a side perspective view of the cover portion of the steriliser of FIG. 1.

The cover portion 14 is shown more clearly in FIG. 2. Cover portion 14 comprises a substantially hemispherical dome body 40 having a rim 42. The dome body 40 can be made of a transparent material, as is shown in the accompanying figures, to allow a user of the steriliser 10 to view the interior of the device when in use.

A plurality of coupling elements 44 are located adjacent the rim 42, projecting from the internal surface of the dome body 40. The coupling elements 44 are located in positions adjacent the rim 42 corresponding to the locations of the locating projections 24 on the coupling collar 20 of the base portion 12.

A hemispherical recess 46 is formed at the apex of the dome body 40, with a handle 48 provided therein.

A plurality of downward-facing steam valves 50 are provided on the dome body 40, located at the rim 42 of the dome body 40. The valves 50 each provide an aperture that projects beyond the external surface of the dome body 40, in a direction away from the apex of the dome body 40.

It will be understood that the inverted dome body 40 may also be used to transfer water to the base portion 12. Visual indicator means are provided in the form of a second raised fill line 19 on the internal surface of the dome body 40. Fill line 19 provides suggestion as to what level of water in the dome body 40 is the appropriate quantity for transferring to the base portion 12. One of the valves 50 can then be used as a pouring spout to easily transfer the water to the base portion 12.

In use, a quantity of water is provided in the base portion 12, preferably up to the fill line 18. The items to be sterilised (e.g. infant pacifiers) are arranged on the mounting arms 34 of the mounting portion 28.

The cover portion 14 is then coupled to the base portion 12 of the steriliser 10 by firstly resting the rim 42 of the dome body 40 on the shoulder 22 of the coupling collar 20 of the base portion 12. The cover portion 14 is rotated in place on the shoulder 22 until the coupling elements 44 of the dome body 40 come into register with the locating projections 24 of the coupling collar 20. The coupling elements 44 and the locating projections 24 interlock with each other, causing the base portion 12 and the cover portion 14 to be secured to one another.

The steriliser 10 can then be placed in a microwave oven and heated. The contained water is turned into steam, which then sterilises the contain items. In order to prevent a substantial steam build up of steam within the steriliser 10, the valves 50 allow for controlled venting of the contained steam. As the valves 50 face towards the base, and therefore away from any potential users of the steriliser 10, the potential for steam burns is reduced.

As the handle 48 is provided within a recess 46 of the steriliser 10, and is not in contact with the internal surface of the steriliser 10, the amount of heat transferred to the surface of the handle is reduced, preventing any burns that may be caused by manipulating the steriliser 10 by the handle 48.

Also, the downward-facing valves enable a user to drain the steriliser 10 of any heated water that may remain in the unit after use, reducing the potential for injury by superheated water.

It will be understood that the length of the mounting arms 34 may be chosen so that the distal ends of the arms 34 are in close proximity to the internal surface of the dome body 40. This configuration prevents any items that may be hanging from the mounting arms 34, e.g. pacifiers, falling from the mounting arms 34. This enables the device 10 to also be employed as a holding container for transport of enclosed items.

It will be understood that the steriliser 10 can be formed from any microwave-friendly, preferably heat-resistant material.

The invention is not limited to the embodiment described herein but can be amended or modified without departing from the scope of the present invention.

The invention claimed is:

1. A device for sterilising items through steam sterilisation, the device comprising:
    a base portion having a receptacle for receiving a quantity of water;
    a removable cover portion to substantially cover said receptacle; and
    a mounting portion to receive an item to be sterilised, the mounting portion projecting from said base portion and enclosed beneath said cover portion, wherein the device further comprises a plurality of vents located on said cover portion, the vents extending from the interior of the device to the exterior of the device, an external open face of said vents facing downwards in the direction of said base portion, the vents operable to allow steam to exit the device, the vents further operable to allow any excess water to be drained from the device.

2. The device of claim 1, wherein the mounting portion comprises a main body and a plurality of mounting arms projecting from the main body, the mounting arms curved in the direction away from said base portion.

3. The device of claim 2, wherein a receiving channel is defined on each of said plurality of mounting arms, said receiving channel facing away from said base portion, said receiving channel being to receive a portion of said item to be sterilised.

4. The device of claim 2, wherein said plurality of mounting arms projecting from the main body comprises:
    a first plurality of mounting arms arranged about said main body, said first plurality located towards a first free end of said main body; and
    a second plurality of mounting arms arranged about said main body, said second plurality located between said first plurality of mounting arms and said base portion.

5. The device of claim 4, wherein the orientation of said second plurality of mounting arms about said main body is offset from the orientation of said first plurality of mounting arms about said main body.

6. The device of claim 2, wherein said plurality of mounting arms are provided in the form of separate modular components, said plurality of mounting arms releasably coupling to said main body.

7. The device of claim 2, wherein said plurality of mounting arms extend from said main body to a free end adjacent an interior surface of said removable cover portion when said removable cover portion is releasably secured to said base portion.

8. The device of claim 1, wherein the device further comprises a plurality of engaging arms located on said base portion, and a plurality of engaging elements located on said cover portion, the position of the engaging elements on the cover portion corresponding to the location of the engaging arms on the base portion, the engaging arms operable to couple with the engaging elements to releasably secure the cover portion to the base portion.

9. The device of claim 1, wherein the device further comprises a portion of support material located on the underside of the base portion, wherein the support material is non-slip material.

10. The device of claim 1, wherein said vents are provided on said removable cover portion.

11. The device of claim 1, wherein a recess is defined on said removable cover portion, a handle element provided within said recess.

12. The device of claim 11, wherein said handle is insulated from said removable cover portion.

13. The device of claim 1, wherein said removable cover portion is substantially transparent.

14. The device of claim 1, wherein said device is formed of material suitable for use in a microwave.

* * * * *